United States Patent
Maehata et al.

(10) Patent No.: US 10,053,448 B2
(45) Date of Patent: Aug. 21, 2018

(54) SUBSTITUTED TETRAZOLINONES FOR CONTROLLING PLANT DISEASES

(71) Applicant: SUMITOMO CHEMICAL COMPANY, LIMITED, Tokyo (JP)

(72) Inventors: Nao Maehata, Takarazuka (JP); Sadayuki Arimori, Takarazuka (JP)

(73) Assignee: SUMITOMO CHEMICAL COMPANY, LIMITED, Tokyo (JP)

(*) Notice: Subject to any disclaimer, the term of this patent is extended or adjusted under 35 U.S.C. 154(b) by 0 days.

(21) Appl. No.: 15/556,453

(22) PCT Filed: Mar. 28, 2016

(86) PCT No.: PCT/JP2016/059819
§ 371 (c)(1),
(2) Date: Sep. 7, 2017

(87) PCT Pub. No.: WO2016/158821
PCT Pub. Date: Oct. 6, 2016

(65) Prior Publication Data
US 2018/0051008 A1    Feb. 22, 2018

(30) Foreign Application Priority Data

Mar. 31, 2015  (JP) ................. 2015-071181
Nov. 27, 2015  (JP) ................. 2015-231447

(51) Int. Cl.
| | | |
|---|---|---|
| A61K 31/41 | (2006.01) |
| C07D 257/04 | (2006.01) |
| C07D 231/10 | (2006.01) |
| C07D 403/12 | (2006.01) |
| A01N 43/713 | (2006.01) |

(52) U.S. Cl.
CPC ......... *C07D 403/12* (2013.01); *A01N 43/713* (2013.01)

(58) Field of Classification Search
CPC ..... A61K 31/41; C07D 231/10; C07D 257/04
USPC .............................. 514/381; 548/251, 364.1
See application file for complete search history.

(56) References Cited

U.S. PATENT DOCUMENTS

2015/0203511 A1    7/2015    Arimori et al.

FOREIGN PATENT DOCUMENTS

| JP | 9-208565 A | 8/1997 |
| JP | 2015-27978 A | 4/2014 |
| JP | 2014-97979 A | 5/2014 |
| WO | WO 96/36229 A1 | 11/1996 |
| WO | WO 2014/051161 A1 | 4/2014 |

OTHER PUBLICATIONS

International Search Report for PCT/JP2016/059819 dated Jun. 14, 2016.

*Primary Examiner* — Douglas M Willis
(74) *Attorney, Agent, or Firm* — Birch, Stewart, Kolasch & Birch, LLP

(57) ABSTRACT

A tetrazolinone compound represented by formula (1):

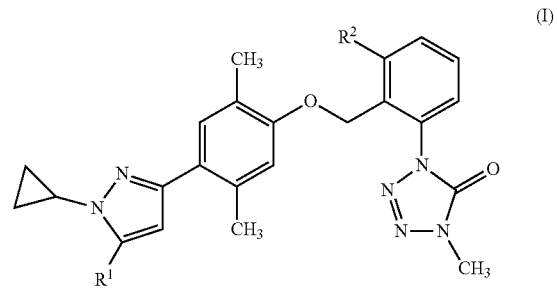

wherein $R^1$ represents a hydrogen atom, a C1-C3 alkyl group optionally having one or more halogen atoms, a C1-C3 alkoxy group optionally having one or more halogen atoms, a halogen atom, a cyano group, or a C1-C3 alkylthio group optionally having one or more halogen atoms; and $R^2$ represents a C1-C3 alkyl group optionally having one or more halogen atoms, a C1-C3 alkoxy group optionally having one or more halogen atoms, a hydrogen atom, a halogen atom, or a C3-C4 cycloalkyl group optionally having one or more halogen atoms, has excellent control activity against plant diseases.

4 Claims, No Drawings

SUBSTITUTED TETRAZOLINONES FOR CONTROLLING PLANT DISEASES

TECHNICAL FIELD

The present invention relates to a plant disease control agent and use thereof.

BACKGROUND OF THE INVENTION

Heretofore, various compounds have been developed so as to control plant diseases (see Patent Document 1).

PRIOR ART DOCUMENT

Patent Document

WO 2014/051165 A

BRIEF SUMMARY OF THE INVENTION

Problems to be Solved by the Invention

An object of the present invention is to provide compounds having excellent control activity against plant diseases.

Means for Solving the Problems

The present inventors have intensively studied so as to find compounds having excellent control activity against plant diseases, and found that a compound represented by formula (I) below has excellent control activity against plant diseases.

The present invention includes the followings.
[1] A tetrazolinone compound represented by formula (1):

(I)

[chemical structure]

wherein $R^1$ represents a hydrogen atom, a C1-C3 alkyl group optionally having one or more halogen atoms, a C1-C3 alkoxy group optionally having one or more halogen atoms, a halogen atom, a cyano group, or a C1-C3 alkylthio group optionally having one or more halogen atoms; and
$R^2$ represents a C1-C3 alkyl group optionally having one or more halogen atoms, a C1-C3 alkoxy group optionally having one or more halogen atoms, a hydrogen atom, a halogen atom, or a C3-C4 cycloalkyl group optionally having one or more halogen atoms (hereinafter referred to as the present compound).
[2] The tetrazolinone compound according to [1], wherein $R^1$ is a hydrogen atom or a C1-C3 alkyl group optionally having one or more halogen atoms.
[3] A plant disease control agent comprising the tetrazolinone compound according to [1] (hereinafter also referred to as the present control agent).

[4] A method for controlling plant diseases, which comprises treating plants or soil with an effective amount of the tetrazolinone compound according to [1].
[5] Use of the tetrazolinone compound according to [1] for controlling plant diseases.

Effects of the Invention

According to the present invention, plant diseases can be controlled.

DETAILED DESCRIPTION OF THE INVENTION

Substituents as used herein will be described below.
The term "optionally having one or more halogen atoms" as used herein means that, when a compound has two or more halogen atoms, these halogen atoms may be the same or different to each other.
For example, the term "C1-C3" as used herein means that the number of carbon atoms is in a range of 1 to 3.
Halogen atom represents a fluorine atom, a chlorine atom, a bromine atom, and an iodine atom.
Aspects of the aspect of the present compound include the following compounds.
A tetrazolinone compound in which $R^1$ is a hydrogen atom in the present compound.
A tetrazolinone compound in which $R^1$ is a hydrogen atom or a methyl group in the present compound.
A tetrazolinone compound in which $R^1$ is a hydrogen atom or a C1-C3 alkyl group in the present compound.
A tetrazolinone compound in which $R^1$ is a hydrogen atom or a C1-C3 alkyl group optionally having one or more halogen atoms in the present compound.
A tetrazolinone compound in which $R^2$ is a methyl group in the present compound.
A tetrazolinone compound in which $R^2$ is a methoxy group in the present compound.
A tetrazolinone compound in which $R^2$ is a methyl group or a methoxy group in the present compound.
A tetrazolinone compound in which $R^2$ is a C1-C3 alkyl group or a C1-C3 alkoxy group in the present compound.
A tetrazolinone compound in which $R^2$ is a C1-C3 alkyl group optionally having one or more halogen atoms or a C1-C3 alkoxy group optionally having one or more halogen atoms in the present compound.
A tetrazolinone compound in which $R^1$ is a hydrogen atom or a methyl group and $R^2$ is a methyl group or a methoxy group in the present compound.
A tetrazolinone compound in which $R^1$ is a hydrogen atom or a C1-C3 alkyl group and $R^2$ is a C1-C3 alkyl group or a C1-C3 alkoxy group in the present compound.
A tetrazolinone compound in which $R^1$ is a hydrogen atom and $R^2$ is a methyl group or a methoxy group in the present compound.
A tetrazolinone compound in which $R^1$ is a methyl group and $R^2$ is a methyl group or a methoxy group in the present compound.
A tetrazolinone compound in which $R^1$ is a hydrogen atom or a methyl group and $R^2$ is a methyl group in the present compound.
A tetrazolinone compound in which $R^1$ is a hydrogen atom or a methyl group and $R^2$ is a methoxy group in the present compound.
A tetrazolinone compound in which $R^1$ is a hydrogen atom or a C1-C3 alkyl group and $R^2$ is a C1-C3 alkyl group, a C1-C3 alkoxy group, a hydrogen atom, a halogen atom, or a C3-C4 cycloalkyl group in the present compound.

A tetrazolinone compound in which $R^1$ is a hydrogen atom or a methyl group and $R^2$ is a methyl group, a methoxy group, a hydrogen atom, a chlorine atom, or a cyclopropyl group in the present compound.

Next, a process for producing the present compound will be described.

The present compound can be produced, for example, by the following Production Processes.

Production Process A

The present compound can be produced by reacting a compound represented by formula (A1) (hereinafter referred to as the compound (A1)) with a compound represented by formula (A2) (hereinafter referred to as the compound (A2)) in the presence of a copper compound and a base:

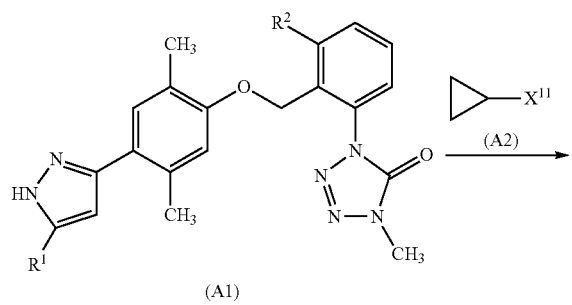

(A1)

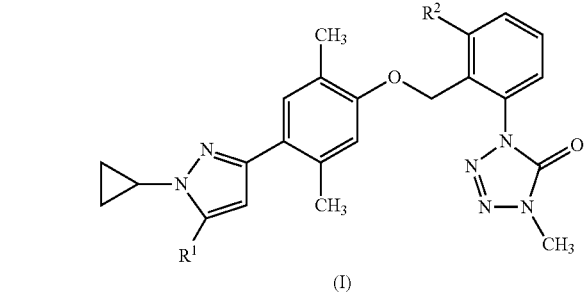

(I)

wherein $X^{11}$ represents a dihydroxyboranyl group, a dialkoxyboranyl group, or a 4,4,5,5-tetramethyl-1,3,2-dioxaborolane-2-yl group, and the other symbols are the same as defined above.

The reaction is usually performed in a solvent.

Examples of the solvent to be used in the reaction include hydrocarbons such as n-hexane, cyclohexane, toluene, and xylene (hereinafter referred to as hydrocarbons); ethers such as diethyl ether, tetrahydrofuran, 1,4-dioxane, ethylene glycol dimethyl ether, methyl tert-butyl ether, and diisopropyl ether (hereinafter referred to as ethers); halogenated hydrocarbons such as chloroform, dichloromethane, and chlorobenzene (hereinafter referred to as halogenated hydrocarbons); acid amides such as dimethylformamide, 1,3-dimethyl-2-imidazolidinone, and N-methylpyrrolidone (hereinafter referred to as acid amides); esters such as ethyl acetate and methyl acetate (hereinafter referred to as esters); sulfoxides such as dimethyl sulfoxide (hereinafter referred to as sulfoxides); nitriles such as acetonitrile and propionitrile (hereinafter referred to as nitriles); alcohols such as methanol, ethanol, propanol, and butanol (hereinafter referred to as alcohols); water; and mixtures thereof.

Examples of the copper compound to be used in the reaction include copper(II) acetate.

Examples of the base to be used in the reaction include organic bases such as triethylamine, pyridine, 2,2'-bipyridine, and diazabicycloundecene (hereinafter referred to as organic bases); and carbonates such as sodium carbonate, sodium hydrogen carbonate, and potassium carbonate.

In the reaction, the compound (A2) is usually used in the proportion within a range of 1 to 10 mols, the copper compound is used in the proportion within a range of 1 to 10 mols, and the base is usually used in the proportion within a range of 1 to 10 mols, based on 1 mol of the compound (A1).

In the reaction, a dehydrating agent such as a Molecular Sieves can be used in the proportion within a range of 100 to 500% by mass based on 1 mol of the compound (A1).

The reaction temperature of the reaction is usually within a range of −20 to 150° C. The reaction time of the reaction is usually within a range of 0.1 to 120 hours.

After completion of the reaction, the present compound can be isolated by performing post-treatment operations such as extraction of the reaction mixture with an organic solvent, and drying and concentration of the organic layer.

The compound (A1) and the compound (A2) are known compounds, or can be produced in accordance with a known method.

Production Process B

The present compound can be produced by reacting a compound represented by formula (A3) (hereinafter referred to as the compound (A3)) with a compound represented by formula (A4) (hereinafter referred to as the compound (A4)) in the presence of a base:

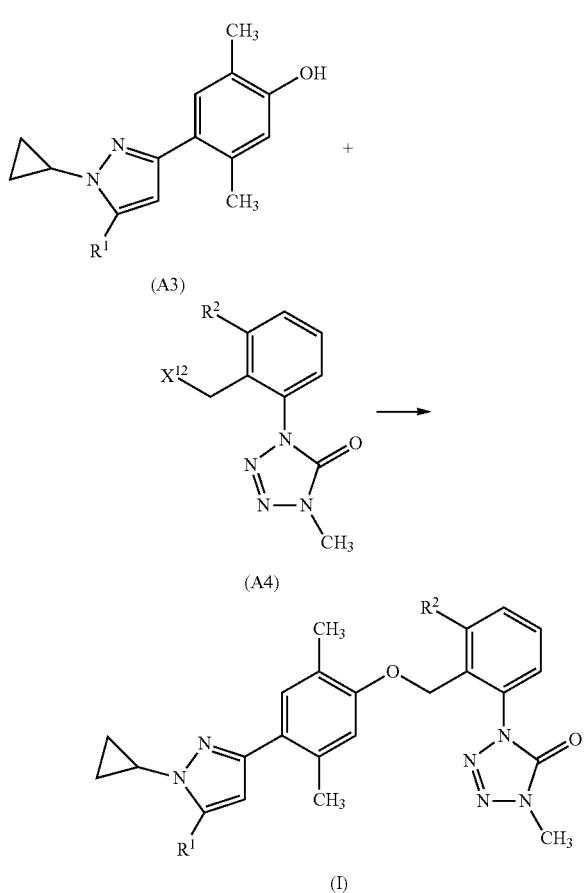

wherein $X^{12}$ represents a chlorine atom, a bromine atom, an iodine atom, a methanesulfonyloxy group, or a p-toluenesulfonyloxy group, and the other symbols are the same as defined above.

The reaction can be produced in accordance with a known method.

Reference Production Process A

A compound represented by formula (B2) (hereinafter referred to as the compound (B2)) can be produced by reacting a compound represented by formula (B1) (hereinafter referred to as the compound (B1)) with the compound (A2) in the presence of a copper compound and a base:

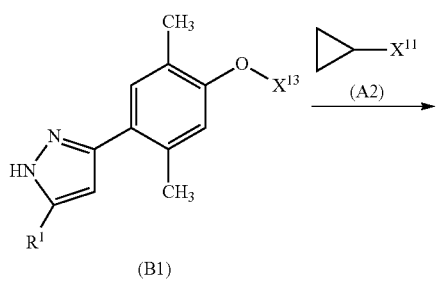

(B1)

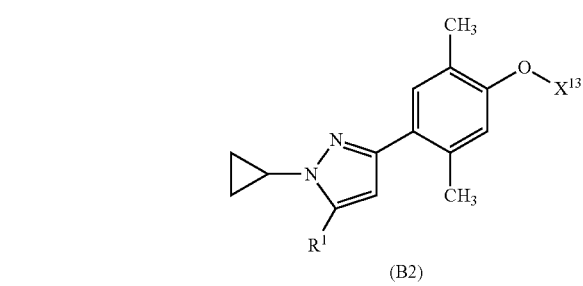

(B2)

wherein $X^{13}$ represents a C1-C5 alkyl group, and the other symbols are the same as defined above.

The reaction can be performed in accordance with the method mentioned in Production Process A.

The compound (B1) is a known compound, or can be produced in accordance with a known method.

Reference Production Process B

The compound (A3) can be produced by reacting the compound (B2) with an acid:

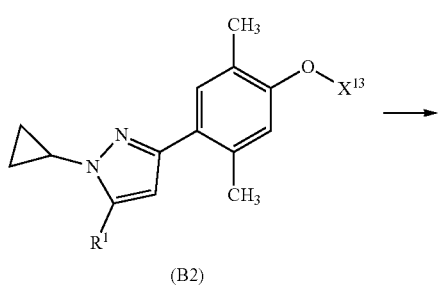

(B2)

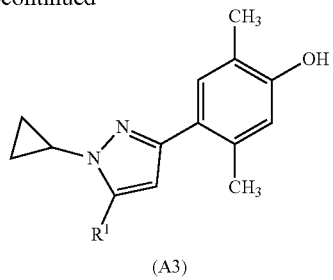

(A3)

wherein the symbols are the same as defined above.

The reaction can be performed by using an acid, etc. in accordance with the method mentioned in WO 2014/051165.

The respective compounds produced by the production processes and reference production process mentioned above sometimes can be isolated and purified by other known means, for example, methods of concentration, concentration under reduced pressure, extraction, partition, crystallization, recrystallization, and chromatography.

Although a form used for the present compound may be the present compound alone, the present compound is usually used after mixing with solid carriers, liquid carriers, surfactants, and the like, and optionally adding auxiliary agents for formulation, such as stickers, dispersers, and stabilizers to thereby formulate into wettable powders, water dispersible granules, flowables, granules, dry flowables, emulsifiable concentrates, aqueous solutions, oil solutions, smoking agents, aerosols, microcapsules, and the like. In these formulations, the present compound is usually contained within a range of 0.1 to 99%, and preferably 0.2 to 90% by weight.

Examples of the solid carriers include clays (for example, kaolin, diatomaceous earth, synthetic hydrated silicon dioxide, Fabism clay, bentonite, and acid clay), talcs or other inorganic minerals (for example, sericite, quartz powder, sulfur powder, activated charcoal, calcium carbonate, and hydrated silica) in the form of fine powders or particulates.

Examples of the liquid carries include water, alcohols, ketones (for example, acetone, methyl ethyl ketone, and cyclohexanone), aromatic hydrocarbons (for example, benzene, toluene, xylene, ethylbenzene, and methyl naphthalene), aliphatic hydrocarbons (for example, n-hexane, and kerosene), esters, nitriles, ethers, acid amides, and halogenated hydrocarbons.

Examples of the surfactants include alkyl sulfates, alkyl sulfonates, alkyl aryl sulfonates, alkyl aryl ethers, and polyoxyethylenated compounds thereof, polyoxyethylene glycol ethers, polyhydric alcohol esters, and sugar alcohol derivatives.

Examples of other auxiliary agents for formulation include stickers, dispersers, and stabilizers, specifically casein, gelatin, polysaccharides (for example, starch, gum arabic, cellulose derivatives, and alginic acid), lignin derivatives, bentonite, saccharides, water-soluble synthetic polymers (for example, polyvinyl alcohol, polyvinylpyrrolidone, and polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, fatty acids or esters thereof, and the like.

The present compound may be used as a mixture with various oils such as mineral oils or vegetable oils, or surfactants. Specific examples of oils or surfactants, which can be used as a mixture with various oils or surfactants, include Nimbus (registered trademark), Assist (registered trademark), Aureo (registered trademark), Iharol (registered trademark), Silwet L-77 (registered trademark), BreakThru (registered trademark), Sundancell (registered trademark), Induce (registered trademark), Penetrator (registered trademark), AgriDex (registered trademark), Lutensol A8 (registered trademark), NP-7 (registered trademark), Triton (registered trademark), Nufilm (registered trademark), Emulgator NP7 (registered trademark), Eula (registered trademark), TRITON X 45 (registered trademark), AGRAL 90 (registered trademark), AGROTIN (registered trademark), ARPON (registered trademark), Unsprayed N (registered trademark), BANOLE (registered trademark), and the like.

The present compound is applied as the present control agent. The method for applying the present control agent is not particularly limited, as long as the applying form is a form by which the present control agent may be applied substantially, and includes, for example, an application to plants such as a foliage application; an application to area for cultivating plants such as a submerged treatment; and an application to soil such as seed disinfection.

The application amount of the present compound in the control method of the present invention varies depending on kinds of plants to be treated, kinds and occurrence frequency of plant diseases to be controlled, formulation forms, application timing, application method, application place, weather conditions, and the like. When applied to stems and leaves of plants, or soil where plants are to be cultivated, the amount of the present compound is usually within a range of 1 to 500 g per 1,000 m$^2$.

The emulsifiable concentrates, gettable powders, and flowables are usually applied after dilution with water. In that case, the concentration of the present compound is usually within a range of 0.0005 to 2% by weight. The dusts, granules, and the like are usually applied as they are without being diluted.

The present compound can be used as an agent for controlling plant diseases in agricultural lands such as fields, paddy fields, lawns, and orchards. The present compound can control diseases occurred in the agricultural lands for cultivating the following "plants".

Crops: corn, rice, wheat, barley, rye, oat, sorghum, cotton, soybean, peanut, buckwheat, beet, rapeseed, sunflower, sugar cane, tobacco, and the like; Vegetables: solanaceous vegetables (for example, eggplant, tomato, pimento, pepper, and potato), cucurbitaceous vegetables (for example, cucumber, pumpkin, zucchini, water melon, and melon), cruciferous vegetables (for example, Japanese radish, white turnip, horseradish, kohlrabi, Chinese cabbage, cabbage, leaf mustard, broccoli, and cauliflower), asteraceous vegetables (for example, burdock, crown daisy, artichoke, and lettuce), liliaceous vegetables (for example, green onion, onion, garlic, and asparagus), umbelliferous vegetables (for example, carrot, parsley, celery, and parsnip), chenopodiaceous vegetables (for example, spinach and Swiss chard), lamiaceous vegetables (for example, *Perilla frutescens*, mint, and basil), strawberry, sweet potato, *Dioscorea japonica, colocasia*, and the like; Flowers; Ornamental foliage plants;

Fruits: pomaceous fruits (for example, apple, pear, Japanese pear, Chinese quince, and quince), stone fruits (for example, peach, plum, nectarine, *Prunus mume*, cherry fruit, apricot, and prune), citrus fruits (for example, Citrus unshiu, orange, lemon, lime, and grapefruit), nuts (for example, chestnut, walnuts, hazelnuts, almond, pistachio, cashew nuts, and macadamia nuts), berry fruits (for example, blueberry, cranberry, blackberry, and raspberry), grape, persimmon, olive, loquat, banana, coffee, date palm, coconuts, and the like;

Trees other than fruit trees: tea, mulberry, flowering plant, roadside trees (for example, ash, birch, dogwood, *Eucalyptus, Ginkgo biloba*, lilac, maple, *Quercus*, poplar, Judas tree, *Liquidambar formosana*, plane tree, *zelkova*, Japanese arborvitae, fir wood, hemlock, juniper, *Pinus, Picea*, and *Taxus cuspidate*); and the like.

The above-mentioned "plants" include genetically modified crops.

Examples of plant diseases which can be controlled by the present compound include plant pathogens such as filamentous fungus and bacteria, and specifically include the following examples, but are not limited thereto.

Rice diseases: blast (*Magnaporthe grisea*), brown spot (*Cochliobolus miyabeanus*), sheath blight (*Rhizoctonia solani*), bakanae disease (*Gibberella fujikuroi*), and downy mildew (*Sclerophthora macrospora*); Wheat diseases: powdery mildew (*Erysiphe graminis*), fusarium blight (*Fusarium gaminearum, F. vacuum, F. culmorum, Microdochium nivale*), rust (*Puccinia striiformis, P. graminis, P. recondita*), pink snow mound (*Micronectriella inhale, M. majus*), typhula snow blight (*Typhula* sp.), loose smut (*Ustilago tritici*), stinking smut (*Tilletia caries, T. controversa*), eyespot (*Pseudocercosporella herpotrichoides*), leaf blotch (*Septoria tritici*), glume blotch (*Stagonospora nodorum*), tan spot (*Pyrenophora tritici-repentis*), seeding blight caused by bacteria of the genus of (*Rhizoctonia solani*), and take-all disease (*Gaeumannomyces graminis*); Barley diseases: powdery mildew (*Erysiphe graminis*), fusarium blight (*Fusarium graminearum, F. avenaceum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), Ramularia disease (*Ramularia collo-cygni*), and seeding blight caused by bacteria of the genus (*Rhizoctonia solani*); Corn diseases: rust (*Puccinia sorghi*), southern rust (*Puccinia polysora*), northern leaf blight (*Setosphaeria turcica*), tropical rust (*Physopella zeae*), southern leaf blight (*Cochliobolus heterostrophus*), anthracnose (*Colletotrichum graminicola*), gray leaf spot (*Cercospora zeae-maydis*), eyespot (*Kabatiella zeae*), phaeosphaeria leaf spot (*Phaeosphaeria maydis*), Diplodia disease (*Stenocarpella maydis, Stenocarpella macrospora*), stalk rot disease (*Fusarium graminearum, Fusarium verticillioides, Colletotrichum graminicola*), and smut (*Ustilago maydis*); Cotton diseases: anthracnose (*Colletotrichum gossypii*), grey mildew (*Ramularia areola*), Alternaria leaf spot (*Alternaria macrospora, A. gossypii*), and Black root rot caused by bacteria from the genus of Thielaviopsis (*Thielaviopsis basicola*); Coffee diseases: rust (*Hemileia vastatrix*), leaf spot (*Cercospora coffeicola*); Rape seed diseases: *sclerotinia* rot (*Sclerotinia sclerotiorum*), black spot (*Alternaria brassicae*), and black leg (*Phoma lingam*); Sugar cane diseases: rust (*Puccinia melanocephala, Puccinia kuehnii*) and smut (*Ustilago scitaminea*); Sunflower diseases: rust (*Puccinia helianthi*) and downy mildew (*Plasmopara halstedii*); Citrus diseases: melanose (*Diaporthe citri*), scab (*Elsinoe fawcetti*), fruit rot (*Penicillium digitatum, P. italicum*), and brown rot (*Phytophthora parasitica, Phytophthora citrophthora*); Apple diseases: blossom blight (*Monilinia mali*), canker (*Valsa ceratosperma*), powdery mildew (*Podosphaera leucotricha*), alternaria leaf spot (*Alternaria alternata* apple pathotype), scab (*Venturia inaequalis*), bitter rot (*Glomerella* cingulata), brown spot (*Diplocarpon mali*), ring spot (*Botryosphaeria berengeriana*), and crown rot (*Phytophthora cactorum*); Pear diseases: scab (*Venturia nashicola, V. pirina*), black star (*Alternaria alternata* Japanese pear pathotype), and rust (*Gymnosporangium haraeanum*); Peach diseases: brown rot (*Monilinia fructicola*), scab (*Cladosporium carpophilum*), and *Phomopsis* rot (*Phomopsis* sp.); Grapes diseases: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), and downy mildew (*Plasmopara viticola*); Japanese persimmon diseases: anthracnose (*Gloeosporium kaki*) and leaf spot (*Cercospora kaki, Mycosphaerella nawae*); Diseases of gourd family: anthracnose (*Colletotrichum lagenarium*), powdery mildew (*Sphaerotheca fuliginea*), gummy stem blight (*Didymella bryoniae*), target spot (*Corynespora cassiicola*), *fusarium* wilt (*Fusarium oxysporum*), downy mildew (*Pseudoperonospora cubensis*), phytophthora rot (*Phytophthora* sp.), and damping-off (*Pythium* sp.); Tomato diseases: early blight (*Alternaria solani*), leaf mold (*Cladosporium fulvum*), leaf mold (*Pseudocercospora fuligena*), and late blight (*Phytophthora infestans*), powdery mildew (*Leveillula taurica*); Eggplant diseases: brown spot (*Phomopsis vexans*) and powdery mildew (*Erysiphe cichoracearum*); Cruciferous vegetables diseases: alternaria leaf spot (*Alternaria japonica*), white spot (*Cercosporella brassicae*), clubroot (*Plasmodiophora brassicae*), and downy mildew (*Peronospora parasitica*); Welsh onion diseases: rust (*Puccinia allii*); Soybean diseases: purple stain (*Cercospora kikuchii*), *sphaceloma* scad (*Elsinoe glycines*), pod and stem blight (*Diaporthe phaseolorum* var. *sojae*), rust (*Phakopsora pachyrhizi*), target spot (*Corynespora cassiicola*), anthracnose (*Colletotrichum glycines, C. truncatum*), *Rhizoctonia* aerial blight (*Rhizoctonia solani*), septoria brown spot (*Septoria glycines*), frog eye leaf spot (*Cercospora sojina*), stem rot (*Sclerotinia sclerotiorum*), powdery mildew (*Microsphaera diffusa*), phytophthora blight (*Phytophthora sojae*), downy mildew (*Peronospora manshurica*), and sudden death syndrome (*Fusarium virguliforme*); Kidney bean diseases: stem rot (*Sclerotinia sclerotiorum*), rust (*Uromyces appendiculatus*), angular leaf spot (*Phaeoisariopsis griseola*), and anthracnose (*Colletotrichum lindemuthianum*); Peanut diseases: early leaf spot (*Cercospora personata*), late leaf spot (*Cercospora arachidicola*), and southern blight (*Sclerotium rolfsii*); Garden pea diseases: powdery mildew (*Erysiphe pisi*); Potato diseases: early blight (*Alternaria solani*), late blight (*Phytophthora infestans*), pink rot (*Phytophthora erythroseptica*), powdery scab (*Spongospora subterranean* f. sp. *subterranea*), and *verticillium* wilt (*Verticillium albo-atrum, V. dahliae, V. nigrescens*); Strawberry diseases: powdery mildew (*Sphaerotheca humuli*); Tea diseases: net blister blight (*Exobasidium reticulatum*), white scab (*Elsinoe leucospila*), gray blight (*Pestalotiopsis* sp.), and anthracnose (*Colletotrichum theae-sinensis*); Tobacco diseases: brown spot (*Alternaria longipes*), anthracnose (*Colletotrichum tabacum*), downy mildew (*Peronospora tabacina*), and black shank (*Phytophthora nicotianae*); Sugar beet diseases: cercospora leaf spot (*Cercospora beticola*), leaf blight (*Thanatephorus cucumeris*), root rot (*Thanatephorus cucumeris*), and *aphanomyces* root rot (*Aphanomyces cochlioides*); Rose diseases: black spot (*Diplocarpon rosae*) and powdery mildew (*Sphaerotheca pannosa*); Chrysanthemum diseases: leaf blight (*Septoria chrysanthemi-indici*) and white rust (*Puccinia horiana*); Onion diseases: *botrytis* leaf blight (*Botrytis cinerea, B. byssoidea, B. squamosa*), gray-mold neck rot (*Botrytis allii*), and small sclerotial rot (*Botrytis squamosa*); various crops diseases: gray mold (*Botrytis cinerea*) and sclerotinia rot (*Sclerotinia sclerotiorum*); Japanese radish diseases: alternaria leaf spot (*Alternaria brassicicola*); Turfgrass diseases: dollar spot (*Sclerotinia homoeocarpa*) and brown patch and large patch (*Rhizoctonia solani*); and Banana diseases: Sigatoka disease (*Mycosphaerella fijiensis, Mycosphaerella musicola*).

Seed diseases or diseases in the early growth phase in various crops caused by bacteria from genera of *Aspergillus, Penicillium, Fusarium, Gibberella, Tricoderma, Thielaviopsis, Rhizopus, Mucor, Corticium, Phoma, Rhizoctonia, Diplodia*, and the like. Viral diseases intermediated by genera of *Polymyxa, Olpidium*, or the like in various crops.

Rice damping-off (*Burkholderia plantarii*); cucumber bacterial blight (*Pseudomonas syringae* pv. *Lachrymans*); eggplant bacterial wilt disease (*Ralstonia solanacearum*), citrus canker (*Xanthomonas citri*); Chinese cabbage soft rod (*Erwinia carotovora*) and the like.

EXAMPLES

The present invention will be more specifically described below by way of Reference Production Examples, Formulation Examples, and Test Examples, but the present invention is not limited to these Examples.

Room temperature as used herein usually means the temperature of 10 to 30° C. $^1$H NMR means a proton nuclear magnetic resonance spectrum. Using tetramethylsilane as an internal standard material, chemical shift (δ) was expressed in ppm.

Production Example 1

A mixture of 0.49 g of the intermediate (1A) mentioned in Reference Production Example 1, 0.31 g of cyclopropylboronic acid, 0.26 g of copper(II) acetate, 0.38 g of pyridine, 0.63 g of Molecular Sieves 4A, and 20 ml of acetonitrile was heated to reflux for 9 hours. The reaction solution was filtered through Celite (registered trademark) and the filtrate was concentrated under reduced pressure. The residue thus obtained was subjected to silica gel column chromatography to obtain 0.33 g of the present compound 1 mentioned below.

Compound produced in accordance with the method mentioned in Production Example 1 and physical properties thereof are shown below.

Compounds Represented by Formula (a):

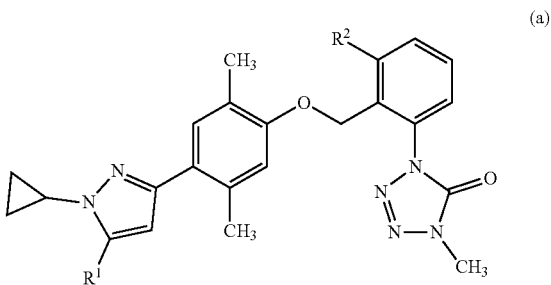

wherein $R^1$ and $R^2$ are shown in [Table 1].

The present compound 1 means a compound represented by formula (a) wherein $R^1$ and $R^2$ are combinations mentioned in the present compound 1 of [Table 1].

TABLE 1

|  | R¹ | R² |
|---|---|---|
| Present Compound 1 | H | OCH₃ |
| Present Compound 2 | H | CH₃ |
| Present Compound 3 | CH₂ | CH₃ |

Present Compound 1:
¹H-NMR (CDCl₃) δ: 7.52-7.41 (3H, m), 7.09-7.06 (2H, m), 6.74 (1H, s), 6.27 (1H, d, J=2.3 Hz), 5.26 (2H, s), 3.93 (3H, s), 3.64-3.60 (1H, m), 3.59 (3H, s), 2.39 (3H, s), 1.97 (3H, s), 1.17-1.13 (2H, m), 1.04-0.99 (2H, m).

Present Compound 2:
¹H-NMR (CDCl₃) δ: 7.44 (1H, d, J=2.3 Hz), 7.42-7.38 (2H, m), 7.31 (1H, s), 7.28 (1H, d, J=2.5 Hz), 6.69 (1H, s), 6.28 (1H, d, J=2.3 Hz), 5.04 (2H, s), 3.64 (3H, s), 3.64-3.59 (1H, m), 2.51 (3H, s), 2.41 (3H, s), 2.06 (3H, s), 1.17-1.14 (2H, m), 1.04-1.01 (2H, m).

Present Compound 3:
¹H-NMR (CDCl₃) δ: 7.43-7.38 (2H, m), 7.29-7.26 (2H, m), 6.67 (1H, s), 6.08 (1H, s), 5.03 (2H, s), 3.64 (3H, s), 3.38-3.32 (1H, m), 2.50 (3H, s), 2.40 (3H, s), 2.39 (3H, s), 2.05 (3H, s), 1.23-1.19 (2H, m), 1.06-1.01 (2H, m).

Production Example 2

A mixture of 0.06 g of the intermediate (11A) mentioned in Reference Production Example 6, 0.08 g of 1-{2-(bromomethyl)phenyl}-4-methyl-1,4-dihydrotetrazol-5-one, 0.04 g of potassium carbonate, and 125 mL of acetonitrile was stirred with heating under reflux for 5 hours. The residue thus obtained was subjected to silica gel column chromatography to obtain 0.08 g of the present compound 4 mentioned below.

Compounds produced in accordance with the method mentioned in Production Example 2 and physical properties thereof are shown below.

Compounds Represented by Formula (a) Wherein R¹ and R² are Shown in [Table 2].

TABLE 2

|  | R¹ | R² |
|---|---|---|
| Present Compound 4 | H | H |
| Present Compound 5 | H | Cl |
| Present Compound 6 | H | c-Pr |

Present Compound 4:
¹H-NMR (CDCl₃) δ: 7.72 (1H, d, J=7.7 Hz), 7.55-7.47 (3H, m), 7.44 (1H, s), 7.34 (1H, s), 6.66 (1H, s), 6.29-6.28 (1H, m), 5.16 (2H, s), 3.68 (3H, s), 3.65-3.59 (1H, m), 2.39 (3H, s), 2.16 (3H, s), 1.18-1.14 (2H, m), 1.04-0.99 (2H, m).

Present Compound 5:
¹H-NMR (CDCl₃) δ: 7.61 (1H, dd, J=8.2, 1.4 Hz), 7.48-7.39 (3H, m), 7.30 (1H, s), 6.71 (1H, s), 6.28 (1H, d, J=2.3 Hz), 5.32 (2H, s), 3.64-3.59 (1H, m), 3.61 (3H, s), 2.41 (3H, s), 2.00 (3H, s), 1.18-1.14 (2H, m), 1.04-0.99 (2H, m).

Present Compound 6:
¹H-NMR (CDCl₃) δ: 7.45-7.41 (2H, m), 7.31 (1H, s), 7.27-7.25 (2H, m), 6.73 (1H, s), 6.29 (1H, d, J=2.3 Hz), 5.26 (2H, s), 3.67-3.59 (1H, m), 3.63 (3H, s), 2.42 (3H, s), 2.15-2.11 (1H, m), 2.05 (3H, s), 1.18-1.14 (2H, m), 1.05-0.97 (4H, m), 0.78-0.74 (2H, m).

Reference Production Examples of intermediates for producing the present compounds mentioned above are shown.

Reference Production Example 1

The intermediate (8A) mentioned in Reference Production Example 3, 40 mL of ethanol, and 8.5 mL of hydrazine monohydrate were added, followed by stirring overnight. Again, the reaction solution was concentrated under reduced pressure and then washed with hexane and tert-butyl methyl ether to obtain 16.2 g of an intermediate (2A) mentioned below.

Compounds produced in accordance with the method mentioned in Reference Production Example 1 and physical properties thereof are shown below.

Compounds Represented by Formula (bA):

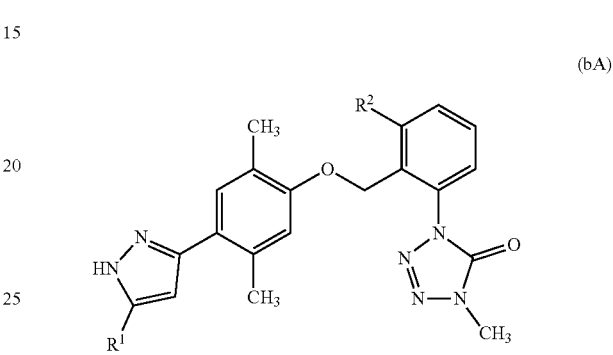

wherein R², R³, Z¹, and Z² are shown in [Table 3].

TABLE 3

|  | R¹ | R² |
|---|---|---|
| Intermediate 1A | H | OCH₃ |
| Intermediate 2A | H | CH₃ |
| Intermediate 3A | CH₃ | CH₃ |

Intermediate (1A):
¹H-NMR (CDCl₃) δ: 7.60 (1H, d, J=2.0 Hz), 7.47 (1H, t, J=8.2 Hz), 7.13-7.06 (3H, m), 6.78 (1H, s), 6.35 (1H, d, J=2.0 Hz), 5.29 (2H, s), 3.95 (3H, s), 3.61 (3H, s), 2.36 (3H, s), 1.98 (3H, s).

Intermediate (2A):
¹H NMR (CDCl₃) δ: 7.62 (1H, d, J=2.0 Hz), 7.43 (2H, m), 7.29 (1H, m), 7.19 (1H, s), 6.73 (1H, s), 6.37 (1H, d, J=1.8 Hz), 5.06 (2H, s), 3.65 (3H, s), 2.52 (3H, s), 2.39 (3H, s), 2.08 (3H, s).

Intermediate (3A):
¹H NMR (CDCl₃) δ: 7.45-7.40 (3H, m), 7.30-7.27 (1H, m), 7.17 (1H, bs), 6.71 (1H, s), 6.13 (1H, s), 5.05 (2H, s), 3.65 (3H, s), 2.52 (3H, s), 2.38 (3H, s), 2.35 (3H, s), 2.07 (3H, s).

Intermediate (4A)

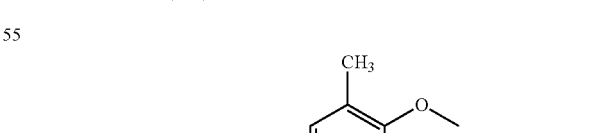

¹H-NMR (CDCl₃) δ: 7.60 (1H, s), 7.21 (1H, s), 6.72 (1H, s), 6.36 (1H, d, J=1.2 Hz), 3.86 (3H, s), 2.40 (3H, s), 2.20 (3H, s).

Reference Production Example 2

A mixture of 15.0 g of 1-(2,5-dimethyl-4-hydroxyphenyl)ethanone, 25.1 g of 1-{2-(bromomethyl)-3-methylphenyl}-4-methyl-1,4-dihydrotetrazol-5-one, 18.1 g of potassium carbonate, and 125 mL of acetonitrile was stirred with heating under reflux for 5 hours. The reaction solution was filtered through Celite (registered trademark) and the filtrate was concentrated under reduced pressure. To the residue, ethyl acetate was added, followed by washing with an aqueous sodium hydrogen carbonate solution. The organic layer was dried over anhydrous magnesium sulfate and then concentrated under reduced pressure to obtain 29.0 g of an intermediate (6A) mentioned below.

Compounds produced in accordance with the method mentioned in Reference Production Example 2 and physical properties thereof are shown below.

Compounds Represented by Formula (cA):

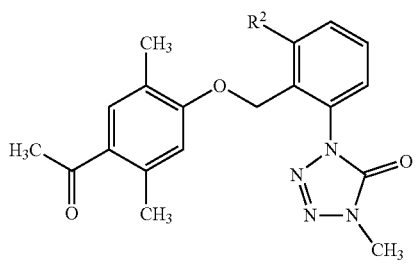

(cA)

wherein $R^2$ is shown in [Table 4].

TABLE 4

|  | $R^2$ |
| --- | --- |
| Intermediate 5A | $OCH_3$ |
| Intermediate 6A | $CH_3$ |

Intermediate (5A):

$^1$H-NMR (CDCl$_3$) δ: 7.50-7.46 (2H, m), 7.11-7.06 (2H, m), 6.73 (1H, s), 5.32 (2H, s), 3.95 (3H, s), 3.62 (3H, s), 2.52 (3H, s), 2.51 (3H, s), 1.98 (3H, s).

Intermediate (6A):

$^1$H-NMR (CDCl$_3$) δ: 7.53 (1H, s), 7.46-7.40 (2H, m), 7.28 (1H, dd, J=7.2, 2.3 Hz), 6.66 (1H, s), 5.08 (2H, s), 3.64 (3H, s), 2.55 (3H, s), 2.53 (3H, s), 2.50 (3H, s), 2.09 (3H, s).

Reference Production Example 3

A mixture of 10 g of the intermediate (5A) and 14 mL of N,N-dimethylformamide diethyl acetal was heated to reflux for 24 hours, and the reaction solution was concentrated under reduced pressure to obtain an intermediate (7A) mentioned below.

Compounds produced in accordance with the method mentioned in Reference Production Example 3 and physical properties thereof are shown below.

Compounds Represented by Formula (dA):

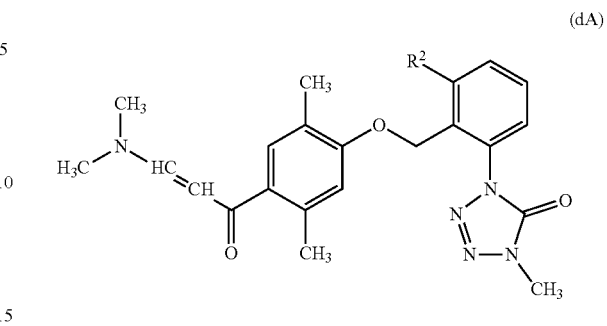

(dA)

wherein $R^2$ is shown in [Table 5].

TABLE 5

|  | $R^2$ |
| --- | --- |
| Intermediate 7A | $OCH_3$ |
| Intermediate 8A | $CH_3$ |

Intermediate (7A):

$^1$H-NMR (CDCl$_3$) δ: 7.47 (1H, t, J=8.3 Hz), 7.41 (1H, s), 7.11-7.05 (3H, m), 6.69 (1H, s), 5.34 (1H, d, J=12.7 Hz), 5.27 (2H, s), 3.94 (3H, s), 3.61 (3H, s), 3.06 (3H, bs), 2.89 (3H, bs), 2.37 (3H, s), 2.21 (3H, s).

Intermediate (8A):

$^1$H-NMR (CDCl$_3$) δ: 7.46-7.40 (3H, m), 7.27 (1H, dd, J=6.7, 2.6 Hz), 7.14 (1H, s), 6.64 (1H, s), 5.35 (1H, d, J=12.7 Hz), 5.04 (2H, s), 3.65 (3H, s), 3.08 (3H, bs), 2.88 (3H, bs), 2.51 (3H, s), 2.39 (3H, s), 1.88 (3H, s).

Reference Production Example 4

To 100 mL of tetrahydrofuran, 2.5 g of 55% sodium hydride and 4.81 g of ethyl acetate were added at room temperature, followed by stirring for 0.5 hour. To the mixture thus obtained, 10.0 g of the intermediate (6A), 0.019 g of dibenzo-18-crown-6, and 1.38 g of ethanol were added, followed by stirring with heating under reflux for 6 hours. Water was added to the reaction mixture, followed by extraction with ethyl acetate. The organic layer was washed with water, dried over anhydrous magnesium sulfate, and then concentrated under reduced pressure to obtain an intermediate (9A) mentioned below.

Intermediate (9A)

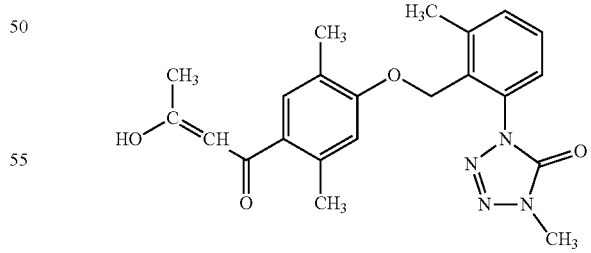

$^1$H-NMR (CDCl$_3$) δ: 7.47-7.40 (3H, m), 7.29 (1H, s), 6.66 (1H, s), 5.84 (1H, s), 5.07 (2H, s), 3.64 (3H, s), 2.50 (3H, s), 2.50 (3H, s), 2.15 (3H, s), 2.06 (3H, s).

Reference Production Example 5

Using the intermediate (4A) in place of the intermediate (1A), compounds were produced in accordance with the method mentioned in Production Example 1 to obtain an intermediate (10A) mentioned below.
Intermediate (10A)

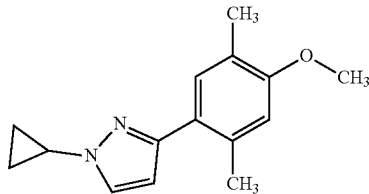 [SMILES: COc1cc(C)c(-c2ccn(C3CC3)n2)cc1C]

$^1$H-NMR (CDCl$_3$) δ: 7.44 (1H, d, J=2.3 Hz), 7.34 (1H, s), 6.68 (1H, s), 6.29 (1H, d, J=2.3 Hz), 3.84 (3H, s), 3.65-3.60 (1H, m), 2.43 (3H, s), 2.20 (3H, s), 1.19-1.15 (2H, m), 1.05-1.00 (2H, m).

Reference Production Example 6

A mixture of 2.00 g of the intermediate (10A), 14 mL of hydrobromic acid, and 14 ml of acetic acid was heated to reflux for 9 hours. The reaction solution was concentrated under reduced pressure. Water was added to the reaction mixture, followed by extraction with ethyl acetate. The residue thus obtained was washed with hexane to obtain 0.54 g of an intermediate (11A) mentioned below.
Intermediate (11A)

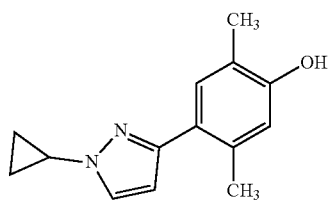 [SMILES: Cc1cc(-c2ccn(C3CC3)n2)c(C)cc1O]

$^1$H-NMR (DMSO-D$_6$) δ: 9.22 (1H, s), 7.74 (1H, d, J=2.3 Hz), 7.21 (1H, s), 6.62 (1H, s), 6.33 (1H, d, J=2.3 Hz), 3.73-3.68 (1H, m), 2.29 (3H, s), 2.09 (3H, s), 1.07-1.03 (2H, m), 0.97-0.92 (2H, m).

In accordance with the method mentioned above, compounds HA101-1 to HA101-96 can be obtained.

HA101-1 to HA101-96 (hereinafter referred to as the present compounds A) mean tetrazolinone compounds mentioned below [in formula, R$^1$ and R$^2$ represent any one of substituent numbers 1 to 96 mentioned below]. In the following [substituent number], c-Pr represents a cyclopropyl group, and CN represents a cyano group. For example, [7; H, CHF$_2$] means that substituent number is 7, R$^1$ is a hydrogen atom, and R$^2$ is a difluoromethyl group.

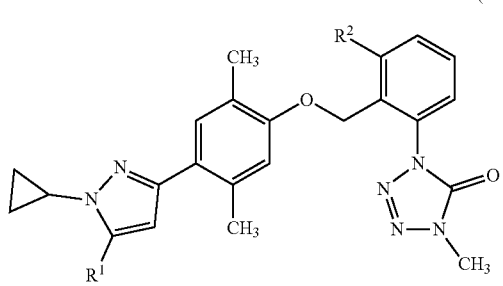

(HA101)

[substituent numbers; R$^1$, R$^2$]
[1; H, H], [2; F, H], [3; Cl, H], [4; CN, H], [5; CH$_3$, H], [6; CH$_2$CH$_3$, H], [7; CHF$_2$, H], [8; CF$_3$, H], [9; OCH$_3$, H], [10; OCH$_2$CH$_3$, H], [11; SCH$_3$, H], [12; SCHF$_2$, H], [13; H, Cl], [14; F, Cl], [15; Cl, Cl], [16; CN, Cl], [17; CH$_3$, Cl], [18; CH$_2$CH$_3$, Cl], [19; CHF$_2$, Cl], [20; CF$_3$, Cl], [21; OCH$_3$, Cl], [22; OCH$_2$CH$_3$, Cl], [23; SCH$_3$, Cl], [24; SCHF$_2$, Cl], [25; H, CH3], [26; F, CH3], [27; Cl, CH3], [28; CN, CH3], [29; CH$_3$, CH3], [30; CH$_2$CH$_3$, CH3], [31; CHF$_2$, CH3], [32; CF$_3$, CH3], [33; OCH$_3$, CH3], [34; OCH$_2$CH$_3$, CH3], [35; SCH$_3$, CH3], [36; SCHF$_2$, CH3], [37; H, CH$_2$ CH$_3$ ], [38; F, CH$_2$ CH$_3$ ], [39; Cl, CH$_2$ CH$_3$ ], [40; CN, CH$_2$ CH$_3$ ], [41; CH$_3$, CH$_2$ CH$_3$ ], [42; CH$_2$ CH$_3$, CH$_2$ CH$_3$ ], [43; CHF$_2$, CH$_2$ CH$_3$ ], [44; CF$_3$, CH$_2$ CH$_3$ ], [45; OCH$_3$, CH$_2$ CH$_3$ ], [46; OCH$_2$ CH$_3$, CH$_2$ CH$_3$ ], [47; SCH$_3$, CH$_2$ CH$_3$ ], [48; SCHF$_2$, CH$_2$ CH$_3$ ], [49; H, CHF$_2$], [50; F, CHF$_2$], [51; Cl, CHF$_2$], [52; CN, CHF$_2$], [53; CH$_3$, CHF$_2$ ], [54; CH$_2$ CH$_3$, CHF$_2$ ], [55; CHF$_2$, CHF$_2$ ], [56; CF$_3$, CHF$_2$ ], [57; OCH$_3$, CHF$_2$ ], [58; OCH$_2$ CH$_3$, CHF$_2$ ], [59; SCH$_3$, CHF$_2$ ], [60; SCHF$_2$, CHF$_2$], [61; H, c-Pr], [62; F, c-Pr], [63; Cl, c-Pr], [64; CN, c-Pr], [65; CH$_3$, c-Pr], [66; CH$_2$CH$_3$, c-Pr], [67; CHF$_2$, c-Pr], [68; CF$_3$, c-Pr], [69; OCH$_3$, c-Pr], [70; OCH$_2$CH$_3$, c-Pr], [71; SCH$_3$, c-Pr], [72; SCHF$_2$, c-Pr], [73; H, OCH$_3$], [74; F, OCH$_3$], [75; Cl, OCH$_3$], [76; CN, OCH$_3$], [77; CH$_3$, OCH$_3$], [78; CH$_2$CH$_3$, OCH$_3$], [79; CHF$_2$, OCH$_3$ ], [80; CF$_3$, OCH$_3$ ], [81; OCH$_3$, OCH$_3$ ], [82; OCH$_2$CH$_3$, OCH$_3$], [83; SCH$_3$, OCH$_3$ ], [84; SCHF$_2$, OCH$_3$], [85; H, OCH$_2$CH$_3$], [86; F, OCH$_2$ CH$_3$ ], [87; Cl, OCH$_2$ CH$_3$ ], [88; CN, OCH$_2$ CH$_3$ ], [89; CH$_3$, OCH$_2$ CH$_3$ ], [90; CH$_2$ CH$_3$, OCH$_2$ CH$_3$], [91; CHF$_2$, OCH$_2$ CH$_3$], [92; CF$_3$, OCH$_2$ CH$_3$], [93; OCH$_3$, OCH$_2$ CH$_3$], [94; OCH$_2$ CH$_3$, OCH$_2$ CH$_3$], [95; SCH$_3$, OCH$_2$ CH$_3$], [96; SCHF$_2$, OCH$_2$CH$_3$]

For example, HA101-7 means a compound represented by formula (HA101) wherein substituent number is 7, which is represented by the following structure.

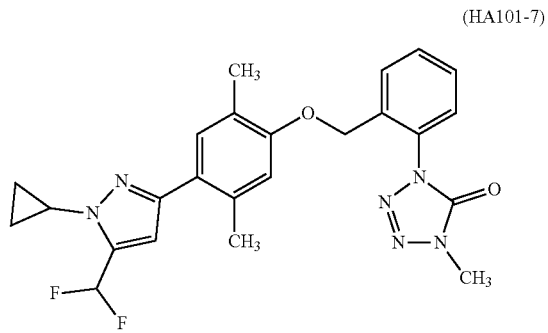 [SMILES: Cc1cc(-c2cc(C(F)F)n(C3CC3)n2)c(C)cc1OCc1ccccc1-n1nnn(C)c1=O]

(HA101-7)

Formulation Examples will be shown below.

Formulation Example 1

Fifty parts (50 parts) of any one of the present compounds A, 3 parts of calcium ligninsulfoate, 2 parts of laurylmagnesium sulfate, and 45 parts of synthetic hydrated silicon oxide are thoroughly ground and mixed to obtain each formulation.

Formulation Example 2

Twenty parts (20 parts) of any one of the present compounds A and 1.5 parts of sorbitan trioleate are mixed with 28.5 parts of an aqueous solution containing 2 parts of polyvinyl alcohol, and the mixture was finely ground by a wet grinding method. Then, 40 parts of an aqueous solution containing 0.05 part of xanthan gum and 0.1 part of aluminum magnesium silicate is added thereto and 10 parts of propylene glycol is further added, followed by stirring and mixing to obtain each formulation.

Formulation Example 3

Two parts (2 parts) of any one of the present compounds A, 88 parts of kaolin clay, and 10 parts of talc are thoroughly ground and mixed to obtain each formulation.

Formulation Example 4

Five parts (5 parts) of any one of the present compounds A, 14 parts of polyoxyethylene styryl phenyl ether, 6 parts of calcium dodecylbenzenesulfonate, and 75 parts of xylene are thoroughly ground and mixed to obtain each formulation.

Formulation Example 5

Two parts (2 parts) of any one of the present compounds A, 1 part of synthetic hydrated silicon oxide, 2 parts of calcium ligninsulfoate, 30 parts of bentonite, and 65 parts of kaolin clay are thoroughly ground and mixed. After the addition of water, the mixture is thoroughly kneaded and further granulated and dried to obtain each formulation.

Formulation Example 6

Twenty parts (20 parts) of any one of the present compounds A, 35 parts of a mixture (weight ratio of 1:1) of white carbon and a polyoxyethylene alkyl ether sulfate ammonium salt, and water are mixed to make 100 parts, followed by a treatment using a grinder to obtain each formulation.

Next, Test Examples will be shown.

The control effect was evaluated by visually observing the area of lesion spots on each of test plants at the time of investigation, and comparing the area of lesion spots on a plant treated with the present compound with that on an untreated plant.

The inhibition rate was evaluated by measuring the absorbance of fungus in a titer plate (with 96 wells) at a wavelength of 550 nm, and using the value obtained from this absorbance as the degree of growth, comparing the degree of growth of each well treated with the present compound with that of an untreated well.

Test Example 1

Each of plastic pots was filled with soil and barley (cultivar: MIKAMO GOLDEN) was sowed and grown in a greenhouse for 7 days. Then, the present compound 1, 2, or 3 formulated in accordance with the method mentioned in Formulation Example 6 was adjusted with water so as to have the concentration of 500 ppm, and then the dilution was sprayed over stems and leaves of the barley so that it sufficiently adhered to the surface of the leaves of the barley. After spraying, the plant was air-dried. After 2 days, an aqueous suspension containing spores of barley net blotch fungus (*Pyrenophora teres*) was sprayed to inoculate the spores. After completion of the inoculation, the plant was left to stand for 3 days in a greenhouse at 23° C. in the daytime and 20° C. at night under high humidity condition and cultivated in a greenhouse for 7 days, and then the area of lesion spots was investigated. As a result, the area of lesion spots on the plant treated with the present compound was 30% or less of that on an untreated plant.

Test Example 2

Each of plastic pots was filled with soil and rice (cultivar: NIHONBARE) was sowed and grown in a greenhouse for 20 days. Then, the present compound 1, 2, or 3 formulated in accordance with the method mentioned in Formulation Example 6 was adjusted with water so as to have the concentration of 500 ppm, and then the dilution was sprayed over stems and leaves of the rice so that it sufficiently adhered to the surface of the leaves of the rice.

After spraying, the plant was air-dried and subjected to a spraying treatment and the rice seedling (cultivar: NIHONBARE) infected by the rice blast fungus (*Magnaporthe grisea*) was left to stand for 6 days at 24° C. in the daytime and 20° C. at night under high humidity condition, while being in contact with each other, and then the area of lesion spots was investigated. As a result, the area of lesion spots on the plant treated with the present compound was 30% or less of that on an untreated plant.

Test Example 3

Each of plastic pots was filled with soil and kidney bean (cultivar: NAGAUZURA SAITO) was sowed and grown in a greenhouse for 8 days. Then, the present compound 1, 2, or 3 formulated in accordance with the method mentioned in Formulation Example 6 was adjusted with water so as to have the concentration of 500 ppm, and then the dilution was sprayed over stems and leaves of the kidney bean so that it sufficiently adhered to the surface of the leaves of the kidney bean. After spraying, the plant was air-dried and a PDA medium containing hyphae of the kidney bean stem rot fungus (*Sclerotinia sclerotiorum*) was placed on the leaves of the kidney bean. After the inoculation, all kidney beans were left to stand under high humidity condition only at night. Four days after the inoculation, the area of lesion spots was investigated. As a result, the area of lesion spots on the plant treated with the present compound was 30% or less of that on an untreated plant.

Test Example 4

Each of plastic pots was filled with soil and wheat (cultivar: APOGEE) was sowed and grown in a greenhouse for 10 days. Then, the present compound 1, 2, or 3 formulated in accordance with the method mentioned in Formulation Example 6 was adjusted with water so as to have the concentration of 500 ppm, and then the dilution was sprayed over stems and leaves of the wheat so that it sufficiently adhered to the surface of the leaves of the wheat. After spraying, the plant was air-dried. After 4 days, an aqueous suspension containing spores of wheat leaf blotch fungus (*Septoria tritici*) was sprayed to inoculate the spores. After completion of the inoculation, the plant was left to stand at 18° C. under high humidity condition for 3 days and left to stand under illumination for 14 to 18 days, and then the area of lesion spots was investigated. As a result, the area of lesion spots on the plant treated with the present compound was 30% or less of that on an untreated plant.

Test Example 5

Each of plastic pots was filled with soil and cucumber (cultivar: SAGAMI HANJIRO) was sowed and grown in a greenhouse for 12 days. Then, the present compound 1, 2, or 3 formulated in accordance with the method mentioned in Formulation Example 6 was adjusted with water so as to have the concentration of 500 ppm, and then the dilution was sprayed over stems and leaves of the cucumber so that it sufficiently adhered to the surface of the leaves of the cucumber. After spraying, the plant was air-dried and then inoculated by sprinkling with spores of cucumber powdery mildew fungus (*Sphaerotheca fuliginea*, a QoI-resistant strain in which, among the genes encoding cytochrome b, the amino acid residue at position 143 of cytochrome b is mutated from glycine to alanine). After the inoculation, the plant was cultivated in a greenhouse at 24° C. in the daytime and 20° C. at night for 8 days, and then the area of lesion spots was investigated. As a result, the area of lesion spots on the plant treated with the present compound was 30% or less of that on an untreated plant.

Test Example 6

Each of plastic pots was filled with soil and wheat (cultivar: SHIROGANE) was sowed and grown in a greenhouse for 9 days. Then, the present compound 1, 2, 3, 4, 5, or 6 formulated in accordance with the method mentioned in Formulation Example 6 was adjusted with water so as to have the concentration of 200 ppm, and then the dilution was sprayed over stems and leaves of the wheat so that it sufficiently adhered to the surface of the leaves of the wheat. After spraying, the plant was air-dried and cultivated at 20° C. for 5 days under illumination, and then inoculated by sprinkling with spores of wheat rust fungus (*Puccinia recondita*). After the inoculation, the plant was left to stand at 23° C. for one day under dark and high humidity condition, and cultivated under illumination at 20° C. for 8 days, and then the area of lesion spots was investigated. As a result, the area of lesion spots on the plant treated with the present compound was 30% or less of that on an untreated plant.

Test Example 7

Each of plastic pots was filled with soil and soybean (cultivar: KUROSENGOKU) was sowed and grown in a greenhouse for 13 days. Then, the present compound 1, 2, 3, 4, or 5 formulated in accordance with the method mentioned in Formulation Example 6 was adjusted with water so as to have the concentration of 200 ppm, and then the dilution was sprayed over stems and leaves of the soybean so that it sufficiently adhered to the surface of the leaves of the soybean. After spraying, the plant was air-dried. After 4 days, an aqueous suspension containing spores of soybean rust fungus (*Phakopsora pachyrhizi*) was sprayed to inoculate the spores. After completion of the inoculation, the plant was left to stand for one day in a greenhouse at 23° C. in the daytime and 20° C. at night under high humidity condition and cultivated in a greenhouse for 14 days, and then the area of lesion spots was investigated. As a result, the area of lesion spots on the plant treated with the present compound was 30% or less of that on an untreated plant.

Test Example 8

Each of plastic pots was filled with soil and barley (cultivar: MIKAMO GOLDEN) was sowed and grown in a greenhouse for 7 days. Then, the present compound 1, 2, 3, 4, 5, or 6 formulated in accordance with the method mentioned in Formulation Example 6 was suspended with water so as to have the concentration of 200 ppm, and then the obtained solution was sprayed over stems and leaves of the barley so that it sufficiently adhered to the surface of the leaves of the barley. After spraying, the plant was air-dried. After 2 days, an aqueous suspension containing spores of barley net blotch fungus (*Rhynchosporium secalis*) was sprayed to inoculate the spores. After completion of the inoculation, the plant was left to stand for 3 days in a greenhouse at 23° C. in the daytime and 20° C. at night under high humidity condition and cultivated in a greenhouse for 7 days, and then the area of lesion spots was investigated. As a result, the area of lesion spots on the plant treated with the present compound was 30% or less of that on an untreated plant.

Test Example 9

Each of plastic pots was filled with soil and cucumber (cultivar: SAGAMI HANJIRO) was sowed and grown in a greenhouse for 19 days. Then, the present compound 1, 2, 3, 4, or 5 formulated in accordance with the method mentioned in Formulation Example 6 was adjusted with water so as to have the concentration of 200 ppm, and then the dilution was sprayed over stems and leaves of the cucumber so that it sufficiently adhered to the surface of the leaves of the cucumber. After spraying, the plant was air-dried. After one day, an aqueous suspension containing spores of cucumber corynespora leaf spot fungus (*Corynespora cassiicola*) was sprayed to inoculate the spores. After the inoculation, the plant was cultivated in a greenhouse at 24° C. in the daytime and 20° C. at night under high humidity condition for 7 days, and then the area of lesion spots was investigated. As a result, the area of lesion spots on the plant treated with the present compound was 30% or less of that on an untreated plant.

Test Example 10

Each of plastic pots was filled with soil and cucumber (cultivar: SAGAMI HANJIRO) was sowed and grown in a greenhouse for 19 days. Then, the present compound 1, 2, 3, 4, 5, or 6 formulated in accordance with the method mentioned in Formulation Example 6 was adjusted with water so as to have the concentration of 200 ppm, and then the dilution was sprayed over stems and leaves of the cucumber so that it sufficiently adhered to the surface of the leaves of the cucumber. After spraying, the cucumber was air-dried. After one day, an aqueous suspension containing spores of cucumber anthrax fungus (*Colletotrichum lagenarium*) was sprayed to inoculate the spores. After the inoculation, the plant was left to stand for one day under high humidity condition and cultivated in a greenhouse at 24° C. in the daytime and 20° C. at night for 6 days, and then the area of lesion spots was investigated. As a result, the area of lesion spots on the plant treated with the present compound was 30% or less of that on an untreated plant.

Test Example 11

Each of plastic pots was filled with soil and cucumber (cultivar: SAGAMI HANJIRO) was sowed and grown in a greenhouse for 19 days. Then, the present compound 1, 2, or 3 formulated in accordance with the method mentioned in Formulation Example 6 was adjusted with water so as to have the concentration of 200 ppm, and then the dilution was sprayed over stems and leaves of the cucumber so that it sufficiently adhered to the surface of the leaves of the cucumber. After spraying, the plant was air-dried. After one day, an aqueous suspension containing zoospores of cucumber downy mildew fungus (*Pseudoperonospora cubensis*) was sprayed to inoculate the zoospores. After the inoculation, the plant was left to stand for one day at 23° C. under high humidity condition and cultivated in a greenhouse at 24° C. in the daytime and 20° C. at night for 6 days, and then the area of lesion spots was investigated. As a result, the area of lesion spots on the plant treated with the present compound was 30% or less of that on an untreated plant.

Test Example 12

Each of plastic pots was filled with soil and soybean (cultivar: TACHINAGAHA) was sowed and grown in a greenhouse for 13 days. Then, an aqueous suspension containing spores of soybean frog eye leaf spot fungus (*Cercospora sojina*) was sprayed to inoculate the spores. After completion of the inoculation, the plant was left to stand for 4 days in a greenhouse at 23° C. under high humidity condition. Five days after the inoculation, the present compound 1, 2, 3, 4, 5, or 6 formulated in accordance with the method mentioned in Formulation Example 6 was adjusted with water so as to have the concentration of 200 ppm, and then the dilution was sprayed over stems and leaves of the soybean so that it sufficiently adhered to the surface of the leaves of the soybean. After spraying, the plant was air-dried and cultivated in a greenhouse for 14 days, and then the area of lesion spots was investigated. As a result, the area of lesion spots on the plant treated with the present compound was 30% or less of that on an untreated plant.

Test Example 13

Each of plastic pots was filled with soil and cucumber (cultivar: SAGAMI HANJIRO) was sowed and grown in a greenhouse for 14 days. Then, the present compound 1 or 2 formulated in accordance with the method mentioned in Formulation Example 6 was adjusted with water so as to contain 0.25 mg/mL, and the roots of the cucumber seedling were immersed in the obtained solution. After 8 days, a PDA medium containing hyphae of the cucumber stem rot fungus (*Sclerotinia sclerotiorum*) was placed on the leaves of the cucumber. After the inoculation, all cucumbers were left to stand under high humidity condition only at night. Four days after the inoculation, the area of lesion spots was investigated. As a result, the area of lesion spots on the plant treated with the present compound was 30% or less of that on an untreated plant.

Test Example 14

The present compound 1, 2, 3, 4, 5, or 6 was diluted with dimethyl sulfoxide so as to obtain a dilution having a concentration of 150 ppm and the dilution thus obtained was suspended into each well of a titer plate (with 96 wells) in the amount of 1 µL, and then 150 µL of a potato dextrose broth liquid medium (PDB medium) inoculated in advance with spores of tomato leaf mold fungus (*Cladosporium fulvum*, a QoI-resistant strain in which, among the genes encoding cytochrome b, the amino acid residue at position 129 of cytochrome b is mutated from phenylalanine to leucine) was added. This plate was cultured at 18° C. for 6 days, thereby allowing tomato leaf mold fungus to undergo proliferation, and then the absorbance at 550 nm of each well of the titer plate was measured, and the value obtained from this absorbance was calculated as the degree of growth of tomato leaf mold fungus. Based on the degree of growth, the inhibition rate was calculated by the following equation.

Inhibition rate=100×($A-B$)/$A$

A: Degree of growth of fungus in untreated area; and
B: Degree of growth of fungus in treated area.

As a result, the inhibition rate of each well treated with the present compound was 80% or more.

Test Example 15

Each of plastic pots was filled with soil and barley (cultivar: MIKAMO GOLDEN) was sowed and grown in a greenhouse for 7 days. Then, the present compound 1, 2, 3, 4, 5, or 6 formulated in accordance with the method mentioned in Formulation Example 6 was adjusted with water so as to have the concentration of 200 ppm, and then the dilution was sprayed over stems and leaves of the barley so that it sufficiently adhered to the surface of the leaves of the barley. After spraying, the plant was air-dried. After 2 days, an aqueous suspension containing spores of barley net blotch fungus (*Pyrenophora teres*) was sprayed to inoculate the spores. After completion of the inoculation, the plant was left to stand for 3 days in a greenhouse at 23° C. in the daytime and 20° C. at night under high humidity condition and cultivated in a greenhouse for 7 days, and then the area of lesion spots was investigated. As a result, the area of lesion spots on the plant treated with the present compound was 30% or less of that on an untreated plant.

Test Example 16

Each of plastic pots was filled with soil and rice (cultivar: NIHONBARE) was sowed and grown in a greenhouse for 20 days. Then, the present compound 1, 2, 3, 4, 5, or 6 formulated in accordance with the method mentioned in Formulation Example 6 was adjusted with water so as to have the concentration of 200 ppm, and then the dilution was sprayed over stems and leaves of the rice so that it sufficiently adhered to the surface of the leaves of the rice. After spraying, the plant was air-dried and subjected to a spraying treatment and the rice seedling (cultivar: NIHONBARE) infected by the rice blast fungus (*Magnaporthe grisea*) was left to stand for 6 days at 24° C. in the daytime and 20° C. at night under high humidity condition, while being in contact with each other, and then the area of lesion spots was investigated. As a result, the area of lesion spots on the plant treated with the present compound was 30% or less of that on an untreated plant.

Test Example 17

Each of plastic pots was filled with soil and kidney bean (cultivar: NAGAUZURA SAITO) was sowed and grown in a greenhouse for 8 days. Then, the present compound 1, 2, 3, 4, or 5 formulated in accordance with the method mentioned in Formulation Example 6 was adjusted with water so as to have the concentration of 200 ppm, and then the dilution was sprayed over stems and leaves of the kidney bean so that it sufficiently adhered to the surface of the leaves of the kidney bean. After spraying, the plant was air-dried and a PDA medium containing hyphae of the kidney bean stem rot fungus (*Sclerotinia sclerotiorum*) was placed on the leaves of the kidney bean. After the inoculation, all kidney beans were left to stand under high humidity condition only at night. Four days after the inoculation, the area of lesion spots was investigated. As a result, the area of lesion spots on the plant treated with the present compound was 30% or less of that on an untreated plant.

Test Example 18

Each of plastic pots was filled with soil and wheat (cultivar: APOGEE) was sowed and grown in a greenhouse for 10 days. Then, the present compound 1, 2, 3, 4, 5, or 6 formulated in accordance with the method mentioned in Formulation Example 6 was adjusted with water so as to have the concentration of 200 ppm, and then the dilution was sprayed over stems and leaves of the wheat so that it sufficiently adhered to the surface of the leaves of the wheat. After spraying, the plant was air-dried. After 4 days, an aqueous suspension containing spores of wheat leaf blotch fungus (*Septoria tritici*) was sprayed to inoculate the spores. After completion of the inoculation, the plant was left to stand at 18° C. under high humidity condition for 3 days and left to stand under illumination for 14 to 18 days, and then the area of lesion spots was investigated. As a result, the area of lesion spots on the plant treated with the present compound was 30% or less of that on an untreated plant.

Test Example 19

Each of plastic pots was filled with soil and cucumber (cultivar: SAGAMI HANJIRO) was sowed and grown in a greenhouse for 12 days. Then, the present compound 1, 2, 3, 4, 5, or 6 formulated in accordance with the method mentioned in Formulation Example 6 was adjusted with water so as to have the concentration of 200 ppm, and then the dilution was sprayed over stems and leaves of the cucumber so that it sufficiently adhered to the surface of the leaves of the cucumber. After spraying, the plant was air-dried and then inoculated by sprinkling with spores of cucumber powdery mildew fungus (*Sphaerotheca fuliginea*, a QoI-resistant strain in which, among the genes encoding cytochrome b, the amino acid residue at position 143 of cytochrome b is mutated from glycine to alanine). After the inoculation, the plant was cultivated in a greenhouse at 24° C. in the daytime and 20° C. at night for 8 days, and then the area of lesion spots was investigated. As a result, the area of lesion spots on the plant treated with the present compound was 30% or less of that on an untreated plant.

INDUSTRIAL APPLICABILITY

The present compound has control activity against plant diseases and is useful as an active ingredient of a plant disease control agent.

The invention claimed is:
1. A compound represented by formula (1):

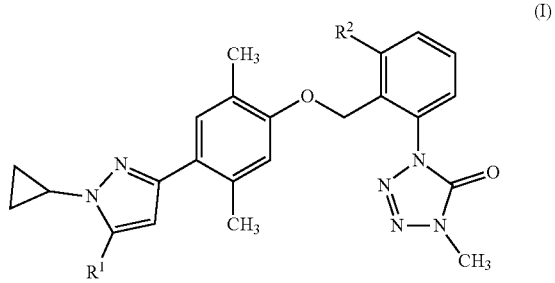

wherein:
R$^1$ represents hydrogen, halogen, cyano, C$_1$-C$_3$ alkyl, C$_1$-C$_3$ alkoxy or C$_1$-C$_3$ alkylthio, wherein C$_1$-C$_3$ alkyl, C$_1$-C$_3$ alkoxy and C$_1$-C$_3$ alkylthio are each optionally substituted with one or more halogens; and
R$^2$ represents hydrogen, halogen, C$_1$-C$_3$ alkyl, C$_1$-C$_3$ alkoxy or C$_3$-C$_4$ cycloalkyl, wherein C$_1$-C$_3$ alkyl, C$_1$-C$_3$ alkoxy and C$_3$-C$_4$ cycloalkyl are each optionally substituted with one or more halogens.

2. The compound according to claim 1, wherein R$^1$ represents hydrogen or optionally substituted C$_1$-C$_3$ alkyl.

3. A formulation comprising a compound according to claim 1 and a phytopathologically acceptable adjuvant, diluent, carrier or excipient.

4. A method for controlling plant diseases, wherein the method comprises treating plants or soil with a phytopathologically effective amount of a compound represented by formula (1):

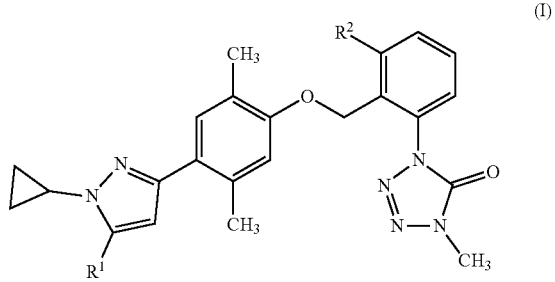

wherein:
R$^1$ represents hydrogen, halogen, cyano, C$_1$-C$_3$ alkyl, C$_1$-C$_3$ alkoxy or C$_1$-C$_3$ alkylthio, wherein C$_1$-C$_3$ alkyl, C$_1$-C$_3$ alkoxy and C$_1$-C$_3$ alkylthio are each optionally substituted with one or more halogens; and
R$^2$ represents hydrogen, halogen, C$_1$-C$_3$ alkyl, C$_1$-C$_3$ alkoxy or C$_3$-C$_4$ cycloalkyl, wherein C$_1$-C$_3$ alkyl C$_1$-C$_3$ alkoxy and C$_3$-C$_4$ cycloalkyl are each optionally substituted with one or more halogens.

* * * * *